United States Patent [19]

Foley

[11] Patent Number: 4,783,814
[45] Date of Patent: Nov. 8, 1988

[54] STETHOSCOPE HAVING PSEUDOSTEREOPHONIC BINAURAL ENHANCEMENT

[75] Inventor: Kevin P. Foley, Alma, Mich.

[73] Assignee: Comprehensive Health Care Corp. of America, Alma, Mich.

[21] Appl. No.: 917,160

[22] Filed: Oct. 9, 1986

[51] Int. Cl.[4] .............................................. A61B 7/04
[52] U.S. Cl. ...................................... 381/67; 381/17; 381/25; 381/74
[58] Field of Search ................... 381/67, 68.2, 17, 25, 381/74

[56] References Cited

U.S. PATENT DOCUMENTS

| | | | |
|---|---|---|---|
| 3,219,757 | 11/1965 | Palladino | 381/17 |
| 4,063,034 | 12/1977 | Peters | 381/17 |
| 4,239,939 | 12/1980 | Griffis | 381/17 |
| 4,308,424 | 12/1981 | Bice, Jr. | 381/17 |
| 4,359,605 | 11/1982 | Haramoto et al. | 381/17 |
| 4,394,535 | 7/1983 | Bingham et al. | 381/17 |
| 4,489,439 | 12/1984 | Scholz et al. | 381/17 |
| 4,594,731 | 6/1986 | Lewkowicz | 381/67 |
| 4,694,497 | 9/1987 | Kasai et al. | 381/17 |
| 4,706,287 | 11/1987 | Blackmer et al. | 381/17 |

OTHER PUBLICATIONS

Chamberlin, Musical Applications of Microprocessors, 1980, pp. 451-452.
National Semiconductor, Linear Applications, vol. 1, 1970, p. AN32-8.

Primary Examiner—Forester W. Isen
Attorney, Agent, or Firm—Learman & McCulloch

[57] ABSTRACT

A stethoscope having a monophonic electrical sensor which feeds electrical signals corresponding to heart sounds to a transversal filter to produce pseudostereophonic signals at split outputs which may be used to power dual earphones for binaural listening. The electronic processing of the heart sounds in the transversal filter enables the listener to differentiate the different sounds of the heart.

9 Claims, 3 Drawing Sheets

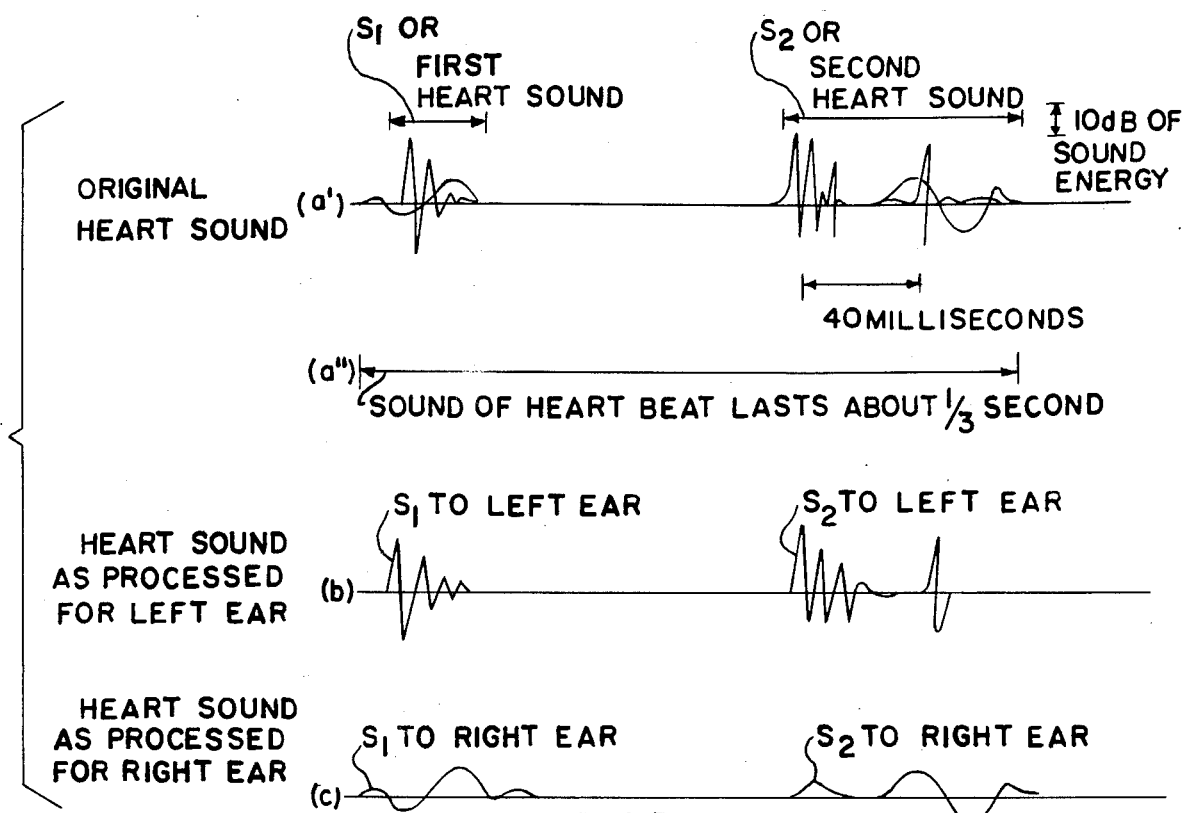
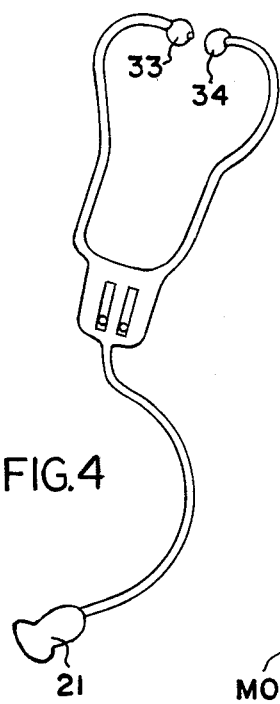
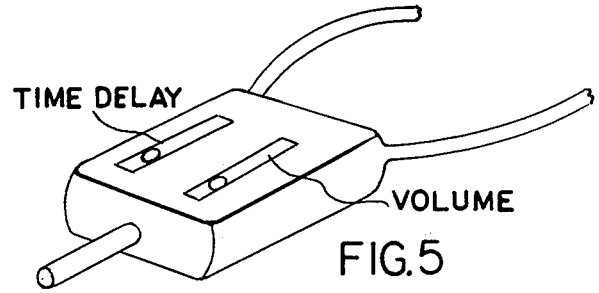
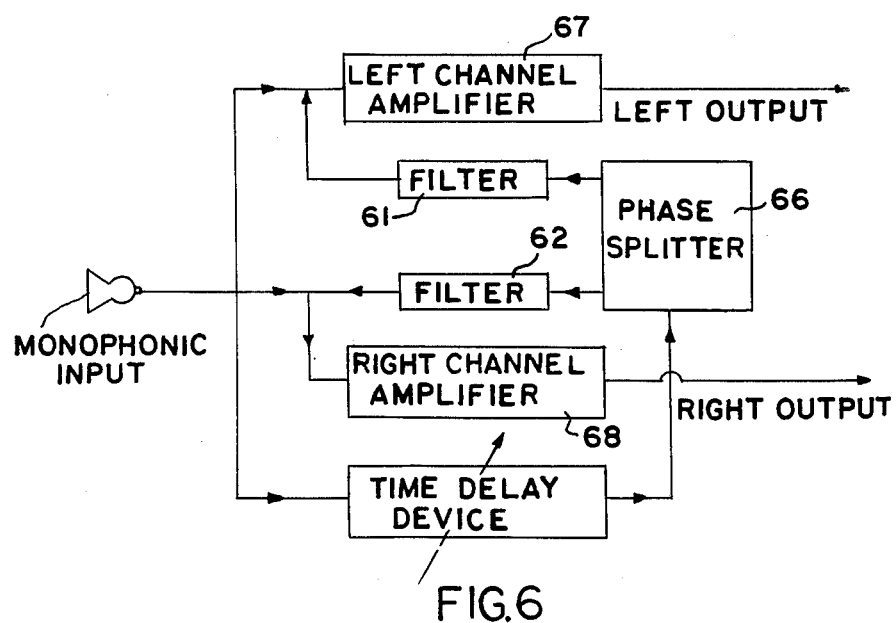
FIG. 3
FIG. 4
FIG. 5
FIG. 6

4,783,814

STETHOSCOPE HAVING PSEUDOSTEREOPHONIC BINAURAL ENHANCEMENT

This invention relates to stethoscopes and more particularly to a stethoscope capable of converting monaural sound to binaural sound.

BACKGROUND OF THE INVENTION

Stethoscopes are used in clinical medicine to listen to heart sounds, lung sounds, and to measure blood pressure through the detection of vascular sounds. In all these applications a single acoustic pickup is sealed to a hose that conveys the information to both ears of a listener simultaneously.

Previous attempts have been made to improve the quality of the transmission of heart sounds, not only through electronic amplification, but also through processing of the heart sound. These attempts have included fairly simple acoustic delays by the use of longer tubing on one channel as is illustrated in U.S. Pat. Nos. 1,817,489; to W. B. Jones, 2,209,164; to W. J. Kerr, and 3,790,711 to Ojima et al. The latter patent also discloses the use of a woofer and tweeter speaker in connection with acoustic delays in tubing.

A very elaborate instrument with complex electronic storage for providing a slowed-down version of an original sound is disclosed in H. V. Katz U.S. Pat. No. 4,528,689. If two sound sensing elements are employed for heart sounds, as in the above identified patent to Kerr, the resulting phase differences in the pickup can cause degradation of the quality of the perceived heart sounds.

Cardiac examination relies extensively on auscultation, that is, the art of listening to heart sounds. As part of a physical examination, the examiner listens to heart sounds, extra sounds, and murmurs such as noises produced by turbulent blood flow. This information conventionally is relayed from the patient's chest to the examiner's ears through one or two stethoscope tubes and presented simultaneously to both ears. Using this method, an average examiner can discriminate a minimum interval between separate sounds of about 40 milliseconds. That is, any two sounds separated by less than 40 milliseconds appear to be a single sound.

The stethoscope disclosed herein provides the ability to differentiate between sounds separated by less than about 40 milliseconds and gives improved clarity and definition to transmitted heart sounds.

SUMMARY OF THE INVENTION

When only one ear is used for hearing, or when both ears are used for hearing sounds simultaneously, the average listener cannot distinguish two sounds that are less than about 40 milliseconds apart. Such closely spaced sounds are perceived as one sound. But if the sounds are transmitted separately to the two ears, a listener can differentiate between sounds spaced less than 40 milliseconds apart.

Use is made of this special property of binaural hearing for the purpose of listening to hear sounds with the electronic stethoscope described herein. The stethescope comprises a single microphone pickup for sensing the heart beat in a monaural manner and an electronic circuit for processing the resulting monaural signal, in both the time and frequency domains, to deliver different signals to a left and a right earphone. This generates a pseudostereophonic binaural perception by the listener of such character as to make it easier to distinguish between certain heart sounds. The electronic processing circuits comprise a transversal filter and solid state active circuits.

THE DRAWINGS

FIG. 3 is a series of three graphs, with legends, illustrative of the operation of the stethoscope;

FIG. 4 is a perspective view of a physcial embodiment of the stethoscope;

FIG. 5 is a perspective view of the controls for the stethoscope;

FIG. 6 is a circuit diagram of another embodiment of the stethoscope utilizing conventional filters in the transversal circuits.

DETAILED DESCRIPTION

The stethescope disclosed herein is a self contained, battery powered, electronically amplified stethoscope having a pseudostereophonic sound synthesizing device utilizing a controllable time delay device for the generation of different sounds on two audio channels that are presented independently to each of a listener's ears. The generation and synthesis of two-channeled sound is continuous, in real time, achieved with a simplicity of components, and can be varied by the user or even eliminated if desired. When listening to a patient's heart with the instant stethoscope activated to introduce the pseudostereophonic effect, the examiner's perception is of a widened, clarified, more defined sound. Split heart sounds gain a distinct quality in that the examiner perceives a spatial orientation to the sound that is as if the heart sounds come from within his own head.

Figure 1:
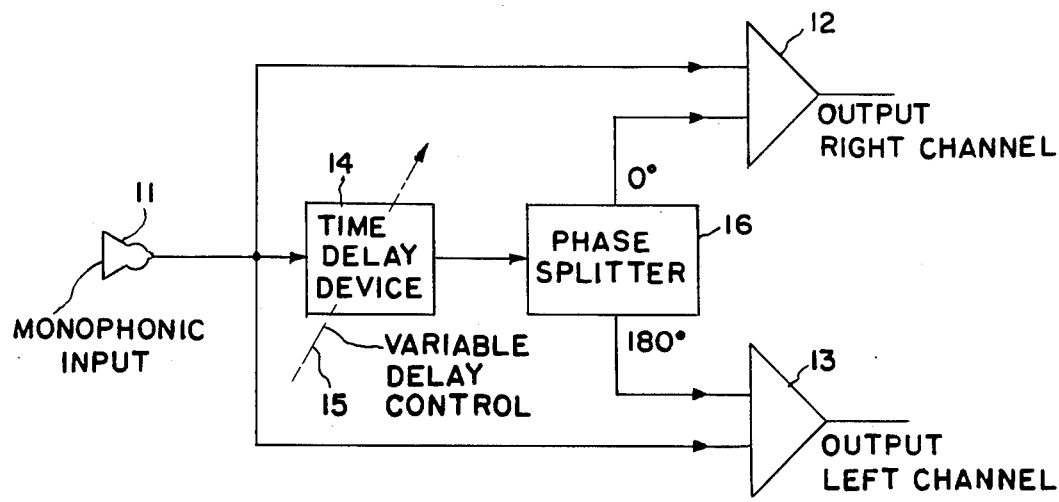
FIG. 1 is a basic box diagram of a stethoscope constructed according to the invention.

A block diagram of the system is shown in FIG. 1. The monophonic input signal from a pick-up microphone 11 is applied directly to a right channel amplifier 12 and to a left channel amplifier 13. It also is applied directly to a variable time delay device 14 which feeds the delayed monophonic input signal directly to a phase splitter 16 that supplies an uninverted signal to the right channel amplifier 12 and an inverted signal to the left channel amplifier 13.

The inputs at the amplifiers 12 and 13 are not labeled to show whether they are the same, as in an adder circuit, or whether they are different, as in a difference amplifier, since either could be used, provided the same type is used for both amplifiers 12 and 13. For purposes of illustration, however, it may be assumed that the two imputs of each of the amplifiers 12 and 13 are noninverting for both the upper input and for the lower input. It also may be assumed that the phase splitter 16 is a transformer having a one-coil primary and a two-coil push-pull secondary with a centertap clamped to a source of fixed voltage, such as ground. The circuit then operates as follows:

The time delay device 14, when the variable delay control 15 is set to give an appreciable delay, produces a delayed signal which is added, via the phase splitter 16, to the direct signal at the right channel amplifier 12. The delayed signal is not heard as a separate sound in the right ear, but changes the apparent sound, without delay, to a different sound. At the same time, the phase splitter 16 transfers an inverted delayed signal to the left channel amplifier 13, where it is added to the direct signal from the microphone 11 to produce a combined signal which produces a combined sound that is different from the original heart sound and also different from the sound transmitted by the right channel amplifier 16. The length of the delay is always less than the amount, about 40 milliseconds, at which the delayed and direct sounds begin to be heard as separate sounds, as in the case of a sound and its echo.

Figure 2:
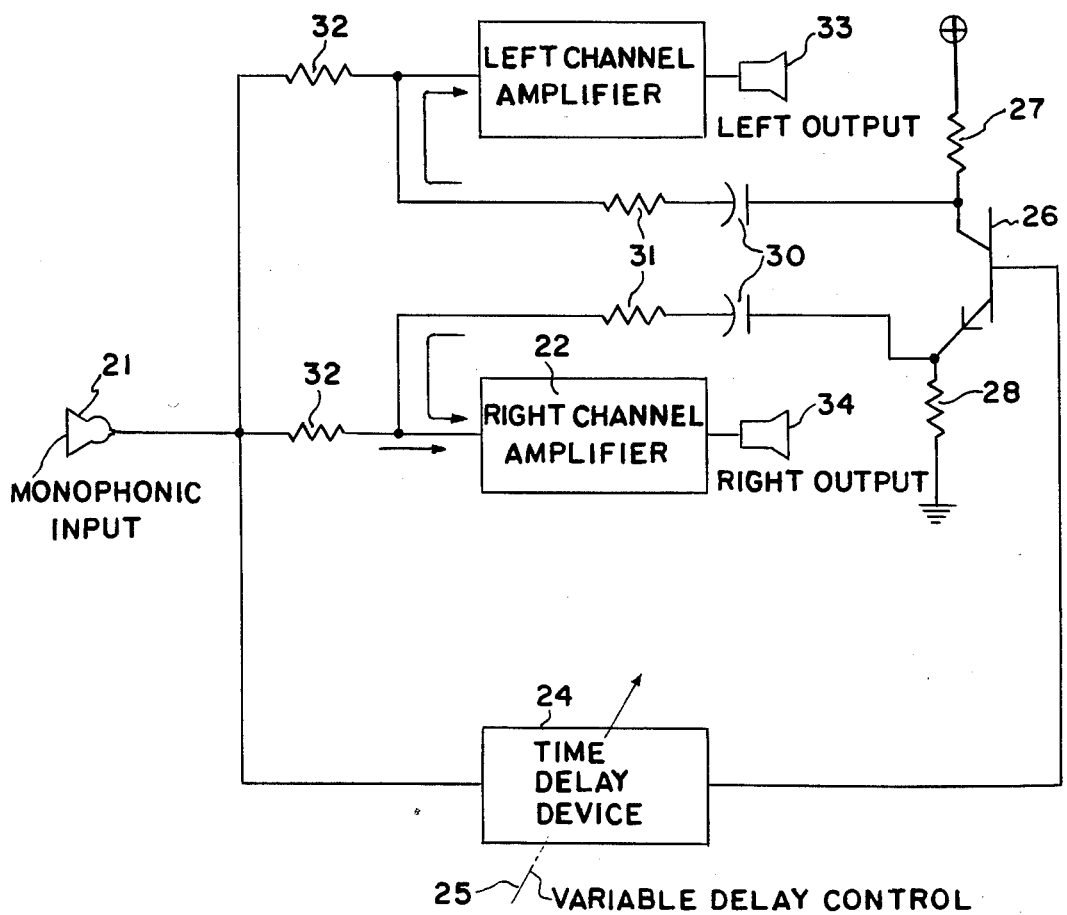
FIG. 2 is a circuit diagram of one embodiment of the stethoscope.

A specific embodiment of the stethoscope diagrammatically shown in FIG. 1 is illustrated in FIG. 2, wherein the phase splitter is in the form of a transistor 26 having corresponding resistors 27 and 28 in the collector circuit and in the emitter circuit, respectively. Under these circumstances, the transistor 26 does not act as a voltage amplifier, but functions as a source of uninverted and inverted duplicates of the time-delayed signal from time delay device 24, as adjusted by a variable delay control 25.

The inverted output from the resister 27 is coupled by a capacitor 30 to a resistive addition circuit consisting of resistors 31 and 32, and through the resistor 31 to the single input of the left channel amplifier 23. At the same time the direct signal from the monophonic microphone 21 is applied through the resistor 32 of the resistive addition circuit to the same single input of the left channel amplifier. Because the signal from the resistor 27 has been inverted, the result is that the two resistors 31 and 32 act to produce a difference signal at the input of the left channel amplifier 23, which is heard in the left earphone 33.

The output at the emitter of the transistor 26 is uninverted, and proceeds from the resistor 28 through a coupling capacitor 30, and through the resistor 31 of the resistive addition circuit for the right channel to the single input of the right channel amplifier 22. At the same time the direct signal from the monophonic microphone 21 proceeds through the resistor 32 of the resistive addition circuit to the single input of the right channel amplifier 22. The output is heard as an altered or different sound in the right earphone 34, and has a character different from that heard in the left earphone 33.

The 180° out of phase signal, that is, the inverted signal, when algebraically combined with the original signal results in the subtraction or loss of specific frequencies in the left channel. The 0° out of phase signal when combined with the original signal adds to the amplitude of certain frequencies that are summed by the right channel amplifier. The net effect on the listener is the perception of the original sound separated into frequency components heard differently by the right and left ears, thereby giving a depth and spatial quality to the sound.

The frequency characterisitics of sound separation are dependent on the length of the delay caused by the time delay device. For example, a time delay of 0.5 milliseconds produces frequency peaks of right-to-left separation of around 1000 cycles per second. whereas a longer delay produces right-left seapartion at lower frequencies. Thus, the frequency at which peak distinction is produced can be selected by adjustment of the variable delay control 25.

The delay control 25, shown in box form, is available as an integrated circuit manufactured by EGG Reticon. It provides a time delay which can be carried from between 0.5 to 2.0 milliseconds under model numbers SAD 512 and SAD 1024, the latter providing more resolution (fine detail of the delayed waveform) than the former.

FIG. 3 is a series of graphs which set off the original heart sound against the sound heard in the right and left ears. Graph a includes a simplified representation in part a'', of a single heart beat which produces a sound that may be heard for about $\frac{1}{3}$ second. This sound has both low and high frequency components, as is shown in part a'. The sound heard is in two parts and is sometimes mimicked by "lub-dub." The "lub" is the first heart sound $S_1$, while the "dub" is the second heart sound $S_2$. The first sound $S_1$ occurs at the time of closure of the atrioventricular valves of the heart. The second sound $S_2$ occurs at the time of closure of the aortic and pulmonic valves.

Graph b shows approximately what is heard by the examiner's left ear and graph c shows what is heard by the examiner's right ear. The net effect on the listener is the perception of a clear and distinct separation of each heart sound within its components. This separation is not heard as a distinct interval in time but is perceived with great clarity of sound with the components of the heart sound seemingly happening within the examiner's head.

It will be noted that the low and the high frequency components of the original heart sounds, which are mixed together in part a' of graph a, are separated in graphs b and c. These graphs help to explain why heart sounds may be distinguished better using a stethoscope constructed according to the invention than when using a conventional stethoscope. Since the graphs concern perception, which cannot be documented directly, they are in part conjectural for purposes of elucidation of the invention. At any rate, the theory set forth is not relied upon as the core of the invention, but only as a plausible basis for explaining the real advantages obtained as a result of its use.

FIG. 4 shows a stethescope constructed in accordance with the invention and FIG. 5 shows the control member, located at the middle of FIG. 4. The control member includes a battery which provides energy for the electronics and also all of the circuitry of FIG. 2, the monophonic microphone 21 and the two earphones 33 and 34 excepted. The miniaturization of the apparatus shown in FIG. 5 is achieved by use of modern integrated circuit techniques.

In a mathematical sense only, the transversal filter used herein is equivalent to a conventional L-C-R filter. However, some filter characteristics are easier to achieve in one type of filter than another. In the case of separating the heart sounds, where distortion is purposely introduced to obtain a pseudostereophonic effect, and where high fidelity in the usual audio sense is not a goal, the transversal filter as used herein is simple and makes miniaturization possible at low cost. However, it additional separation of the heart sounds is desirable, the circuit of FIG. 6 can be used. Here conventional fixed filters 61 and 62 such, for example, as high and low pass R-C filters, are inserted into the coupling circuits between the phase splitter 66 and the left and right channel amplifiers 67 and 68, respectively.

Figure 7:
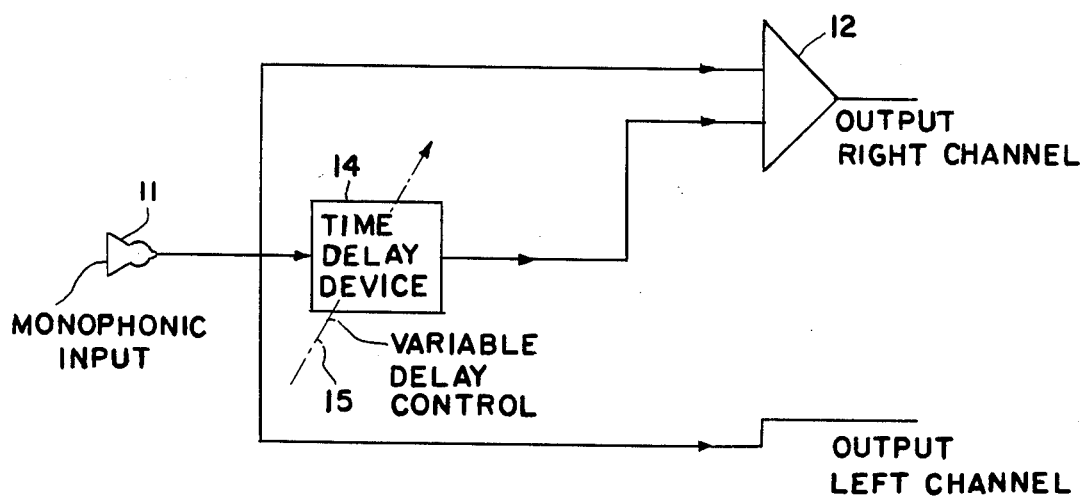
FIG. 7 is a basic box diagram of another embodiment of stethescope that introduces distortion into one ear only.

As disclosed herein the transversal filter is used to produce opposite distortions in both the left and right channels. It should be noted however, that somewhat the same effect is available without the use of a phase splitter, if the distortion of the transversal filter is produced in only one channel while the original microphone signal appears on the other channel (as depicted in FIG. 7). With this possibly more economical system, the distinction between the sounds in the right and left channels, as perceived, is lessened, but is adequate for some purposes.

The disclosed embodiments are representative of presently preferred forms of the invention, but are intened to be illustrative rather than definitive thereof. The invention is defined in the claims.

What is claimed is:

1. A stethoscope for use in listening to body sounds comprising:
   a monophonic microphone for sensing said body sounds and converting said body sounds into a corresponding monophonic signal;
   a right earphone and a left earphone enabling binaural hearing by a user of said stethoscope;
   transversal filter means for converting said corresponding monophonic signal into a corresponding different output signal;
   means for transmitting said corresponding different output signal to only one of said earphones; and
   means for transmitting said corresponding monophonic signal to the other one of said earphones;
   whereby sounds heard in said right and left earphones are different and create a pseudostereophonic effect during binaural hearing by said user.

2. The stethoscope according to claim 1 wherein said transversal filter means comprises time delay means responsive to said corresponding monophonic signal for delaying such signal by a selected amount, and means for algebraically combining the delayed signal with said corresponding monophonic signal to produce said corresponding different output signal.

3. The stethoscope according to claim 2 whrrein the delay means is adjustable to provide a selected delay.

4. The stethoscope according to claim 3 wherein the time delay is adjustable over a range from substantially zero to 40 milliseconds.

5. A stethoscope for listening to body sounds comprising:
   a monophonic microphone for sensing said body sounds and converting them into a corresponding monphonic signal;
   a right earphone and a left earphone enabling binaural hearing by a user of said stethoscope;
   transversal filter means for converting said corresponding monophonic signal into two different corresponding output signals; and
   means for individually connecting said two different corresponding output signals to respective ones of said right and left earphones to produce different sounds for said right and left earphones;
   whereby the different sounds heard in said right and left earphones create a pseudostereophonic effect during binaural hearing by said user.

6. The stethoscope according to claim 5 wherein said transversal filter means comprises time delay means responsive to said corresponding monophonic signal for delaying such signal by a selected amount, means for phase splitting the delayed signal, and means for algebraically combining each of the delayed signals, as split, with said corresponding monophonic signal and thereby produce said two different corresponding output signal.

7. The stethoscope according to claim 6 wherein the time delay means is adjustable to provide a selected length delay.

8. The stethoscope according to claim 7 wherein the time delay is adjustable over a range from substantially zero to 40 milliseconds.

9. The stethoscope according to claim 6 wherein the phase splitter is a transistor having base input, emitter and collector resistors, and output connections from the emitter and collector for supplying the delayed split signals.

* * * * *